(12) United States Patent
Rao et al.

(10) Patent No.: US 9,314,639 B2
(45) Date of Patent: Apr. 19, 2016

(54) TECHNIQUES FOR LOGGING AND USING PROGRAMMING HISTORY IN A NEUROSTIMULATION SYSTEM

(71) Applicant: BOSTON SCIENTIFIC NEUROMODULATION CORPORATION, Valencia, CA (US)

(72) Inventors: Prakash Rao, Philadelphia, PA (US); Anita Yip, Los Angeles, CA (US); Sridhar Kothandaraman, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 14/198,408

(22) Filed: Mar. 5, 2014

(65) Prior Publication Data

US 2014/0277261 A1    Sep. 18, 2014

Related U.S. Application Data

(60) Provisional application No. 61/793,681, filed on Mar. 15, 2013.

(51) Int. Cl.
| | | |
|---|---|---|
| *A61N 1/00* | (2006.01) | |
| *A61N 1/372* | (2006.01) | |
| *A61N 1/378* | (2006.01) | |

(52) U.S. Cl.
CPC .......... *A61N 1/37247* (2013.01); *A61N 1/3787* (2013.01); *A61N 1/37264* (2013.01)

(58) Field of Classification Search
CPC .................................. A61N 1/37235–1/37247
See application file for complete search history.

(56) References Cited

U.S. PATENT DOCUMENTS

| | | | |
|---|---|---|---|
| 5,893,883 | A | 4/1999 | Torgerson et al. |
| 6,478,737 | B2 | 11/2002 | Bardy |
| 6,516,227 | B1 | 2/2003 | Meadows et al. |
| 6,895,280 | B2 | 5/2005 | Meadows et al. |
| 6,993,384 | B2 | 1/2006 | Bradley et al. |
| 7,489,970 | B2 | 2/2009 | Lee et al. |
| 7,840,268 | B2 | 11/2010 | Blischak et al. |
| 7,894,908 | B2 | 2/2011 | Lee et al. |
| 8,095,220 | B2 | 1/2012 | Lee et al. |
| 8,155,749 | B2 | 4/2012 | Lee et al. |
| 2008/0177346 | A1 | 7/2008 | Armstrong |
| 2010/0010566 | A1 | 1/2010 | Thacker et al. |
| 2010/0121409 | A1 | 5/2010 | Kothandaraman et al. |
| 2011/0257707 | A1 | 10/2011 | Kothandaraman |
| 2012/0109230 | A1 | 5/2012 | Kothandaraman et al. |

OTHER PUBLICATIONS

U.S. Appl. No. 61/452,965, Neurostimulation System for Defining a Generalized Ideal Multipole Configuration, Inventor: Dongchul Lee et al., filing date: Mar. 15, 2011.

(Continued)

*Primary Examiner* — Scott Getzow
(74) *Attorney, Agent, or Firm* — Schwegman Lundberg & Woessner, P.A.

(57) ABSTRACT

An external control device, a neurostimulation system, and a method for providing therapy to a patient are provided. A plurality of stimulation parameter sets are defined, electrical stimulation energy is serially conveyed to tissue of the patient in accordance with the plurality of stimulation parameter sets, a historical log file is stored, and the plurality of stimulation parameter sets are logged in the historical log file.

20 Claims, 10 Drawing Sheets

(56) References Cited

OTHER PUBLICATIONS

U.S. Appl. No. 61/486,141, Neurostimulation System with On-Effector Programmer Control, Inventor: Chester Kim et al., filing date: May 13, 2011.

U.S. Appl. No. 61/576,924, Seamless Integration of Different Programming Modes for a Neurostimulator Programming System, Inventor: Sridhar Kothandaraman et al., filing date: Dec. 16, 2011.

TECHNIQUES FOR LOGGING AND USING PROGRAMMING HISTORY IN A NEUROSTIMULATION SYSTEM

RELATED APPLICATION DATA

The present application claims the benefit under 35 U.S.C. §119 to U.S. Provisional Application Ser. No. 61/793,681, filed Mar. 15, 2013. The foregoing application is hereby incorporated by reference into the present application in its entirety.

FIELD OF THE INVENTION

The present invention relates to tissue stimulation systems, and more particularly, to techniques for programming a neurostimulation system.

BACKGROUND OF THE INVENTION

Implantable neurostimulation systems have proven therapeutic in a wide variety of diseases and disorders. Pacemakers and Implantable Cardiac Defibrillators (ICDs) have proven highly effective in the treatment of a number of cardiac conditions (e.g., arrhythmias). Spinal Cord Stimulation (SCS) systems have long been accepted as a therapeutic modality for the treatment of chronic pain syndromes, and the application of tissue stimulation has begun to expand to additional applications such as angina pectoralis and incontinence. Deep Brain Stimulation (DBS) has also been applied therapeutically for well over a decade for the treatment of refractory chronic pain syndromes, and DBS has also recently been applied in additional areas such as movement disorders and epilepsy. Further, in recent investigations, Peripheral Nerve Stimulation (PNS) systems have demonstrated efficacy in the treatment of chronic pain syndromes and incontinence, and a number of additional applications are currently under investigation. Furthermore, Functional Electrical Stimulation (FES) systems, such as the Freehand system by NeuroControl (Cleveland, Ohio), have been applied to restore some functionality to paralyzed extremities in spinal cord injury patients.

These implantable neurostimulation systems typically include one or more electrodes carrying stimulation leads, which are implanted at the desired stimulation site, and a neurostimulator (e.g., an implantable pulse generator (IPG)) implanted remotely from the stimulation site, but coupled either directly to the stimulation lead(s) or indirectly to the stimulation lead(s) via a lead extension. The neurostimulation system may further include an external control device in the form of a remote control to remotely instruct the neurostimulator to generate electrical stimulation pulses in accordance with selected stimulation parameters.

Electrical stimulation energy may be delivered from the neurostimulator to the electrodes in the form of an electrical pulsed waveform. Thus, stimulation energy may be controllably delivered to the electrodes to stimulate neural tissue. The combination of electrodes that are used to deliver electrical pulses to the targeted tissue constitutes an electrode combination, with the electrodes capable of being selectively programmed to act as anodes (positive), cathodes (negative), or turned off (zero). In other words, an electrode combination represents the polarity being positive, negative, or zero. Other parameters that may be controlled or varied include the amplitude, width, and rate of the electrical pulses provided through the electrode array. Each electrode combination, along with the electrical pulse parameters, can be referred to as a "stimulation parameter set."

With some neurostimulation systems, and in particular, those with independently controlled current or voltage sources, the distribution of the current to the electrodes (including the case of the neurostimulator, which may act as an electrode) may be varied such that the current is supplied via numerous different electrode configurations. In different configurations, the electrodes may provide current or voltage in different relative percentages of positive and negative current or voltage to create different electrical current distributions (i.e., fractionalized electrode combinations).

As briefly discussed above, a remote control can be used to instruct the neurostimulator to generate electrical stimulation pulses in accordance with the selected stimulation parameters. Typically, the stimulation parameters programmed into the neurostimulator can be adjusted by manipulating controls on the remote control to modify the electrical stimulation provided by the neurostimulation system to the patient. Thus, in accordance with the stimulation parameters programmed by the remote control, electrical pulses can be delivered from the neurostimulator to the stimulation electrode(s) to stimulate or activate a volume of tissue in accordance with a set of stimulation parameters and provide the desired efficacious therapy to the patient. The best stimulus parameter set will typically be the one that delivers stimulation energy to the volume of tissue that must be stimulated in order to provide the therapeutic benefit (e.g., treatment of pain), while minimizing the volume of non-target tissue that is stimulated.

However, the number of electrodes available combined with the ability to generate a variety of complex stimulation pulses, presents a huge selection of stimulation parameter sets to the clinician or patient. For example, if the neurostimulation system to be programmed has an array of sixteen electrodes, millions of stimulation parameter sets may be available for programming into the neurostimulation system. Today, neurostimulation system may have up to thirty-two electrodes, thereby, exponentially increasing the number of stimulation parameters sets available for programming.

To facilitate such selection, the clinician generally programs the neurostimulator through a computerized programming system. This programming system can be a self-contained hardware/software system, or can be defined predominantly by software running on a standard personal computer (PC). The PC or custom hardware may actively control the characteristics of the electrical stimulation generated by the neurostimulator to allow the optimum stimulation parameters to be determined based on patient feedback or other mechanism and to subsequently program the neurostimulator, and optionally the remote control, with the optimum stimulation parameter set or sets.

One known computerized programming system for SCS is called the Bionic Navigator®, available from Boston Scientific Neuromodulation Corporation. The Bionic Navigator® is a software package that operates on a suitable PC and allows clinicians to program stimulation parameters into an external handheld programmer (referred to as a remote control) and/or the neurostimulator. Each set of stimulation parameters, including fractionalized current distribution to the electrodes (as percentage cathodic current, percentage anodic current, or off), may be stored in both the Bionic Navigator® and the remote control and combined into a stimulation program that can be used to stimulate multiple regions within the patient.

In creating a stimulation parameter set, the Bionic Navigator® may be operated by a clinician in a "manual mode" to manually select the percentage cathodic current and percentage anodic current flowing through the electrodes, or may be operated by the clinician in an "automated mode" to electrically "steer" the current along the implanted leads in real-time (e.g., using a joystick or joystick-like controls), thereby, allowing the clinician to experimentally determine the most efficacious stimulation parameters. Once a polarity and the amplitude (either as an absolute or a percentage) for the current or voltage on an active electrode is selected in a typical computerized programming system, the polarity and amplitude value may be displayed on a display screen in association with this electrode to the user.

Despite the fact that computerized programming systems have been used to speed up the programming process, programming of an electrical stimulation system using present-day computerized programming systems may still be a relatively time-consuming process and may need improvements. For example, as discussed, while programming, the clinician takes feedback from the patient, experimentally navigates, in either "manual mode" or "automated mode," between different stimulation parameter sets to find the most efficacious treatment regimen, and then saves it. At times, a patient may request the clinician to program a previously used treatment regimen, set during a past clinical visit of the patient or set earlier during the course of the experimental navigation in the current clinical visit, as the patient may believe that a previous treatment regimen is more effective than the current treatment regimen. In such cases, programming such a past treatment regimen is difficult for the clinician to recall, as most of the treatment regimens are not saved during experimental navigation due to the large number of stimulation parameter values that are tested during experimental navigation. If the patient requested treatment regimen was not saved earlier, then the clinician may need to cumbersomely find that treatment regimen by experimental navigation again.

There, thus, remains a need for a more efficient means for programming a neurostimulation system.

SUMMARY OF THE INVENTION

In accordance with a first aspect of the present inventions, an external control device for use with a neurostimulator coupled to one or more electrodes implanted within tissue is provided. The external control device comprises a user interface including one or more stimulation parameter controls configured for being actuated by a user to define a plurality of stimulation parameter sets (e.g., at least one includes at least one of a pulse amplitude, a pulse width, a pulse rate, and an electrode combination). In one embodiment, each of the stimulation parameter sets includes fractionalized electrical current values respectively for the electrodes, in which case, the user interface may include a display screen configured for displaying a graphical representation of the plurality of electrodes, and for displaying the fractionalized electrical current values in association with the graphical representation of the plurality of electrodes.

The external control device further comprises memory configured for storing a historical log file, and a controller configured for, in response to an input from the user, instructing the neurostimulator to serially convey electrical stimulation energy to the one or more electrodes in accordance with the plurality of stimulation parameter sets, and logging the plurality of stimulation parameter sets in the historical log file. In an optional embodiment, the controller is configured for logging temporal stamps (e.g., a time stamp and/or date stamp), relative to a start of a therapeutic procedure, or in the historical log file respectively indicating when the plurality of stimulation parameter sets were defined. The temporal stamps may be absolute or may be relative to a start of a therapeutic procedure. The external control device may further comprise output circuitry configured for transmitting instructions to the neurostimulator.

In one optional embodiment, the user interface includes an enable/disable control configured for being actuated by the user to selectively allow the controller to log the plurality of stimulation parameter sets in the historical log file or prevent the controller from logging the plurality of stimulation parameter sets in the historical log file. In another embodiment, the user interface includes a display screen configured for displaying the historical log file. The displayed historical log file may include serial numbers respectively associated with the logged stimulation parameter sets, and corresponding to the order in which the stimulation parameter sets were defined. The displayed historical log file may also include an information icon associated with each of the logged stimulation parameter sets. The information icon may be selectable to access additional information respectively associated with the logged stimulation parameter sets. Each information icon may also be selectable to allow the user to add additional information associated with the respective logged stimulation parameter set.

In another optional embodiment, the user interface may be configured for allowing the user to select one of the logged stimulation parameter sets, and the controller may be further configured for, in response to the selected logged stimulation parameter set, automatically resetting the one or more stimulation parameter controls to define the selected logged stimulation parameter set. The user interface may include a display screen configured for displaying the historical log file as a list, and be further configured for allowing the user to select the logged stimulation parameter set from the displayed list with a pointing device. The user interface may also include an undo control, the actuation of which selects the logged stimulation parameter set immediately defined prior to a stimulation parameter set currently defined by the one or more stimulation parameter controls, and a redo control, the actuation of which selects the logged stimulation parameter set immediately defined subsequent to a stimulation parameter set currently defined by the one or more stimulation parameter controls.

In one embodiment, the user interface includes a directional control device, the actuation of which defines a plurality of predicted stimulation regions relative to the at least one electrode respectively corresponding to the plurality of stimulation parameter sets, the user interface further includes a display screen configured for displaying the historical log file as a trace that spatially connects points respectively corresponding to the predicted stimulation regions, and the user interface is configured for allowing the user to select the logged stimulation parameter set from the displayed trace with a pointing device.

In accordance with a second aspect of the present inventions, a neurostimulation system is provided. The neurostimulation system comprises one or more electrodes, a neurostimulator, a user interface including one or more stimulation parameter controls configured for being actuated by a user to define a plurality of stimulation parameter sets, a memory configured for storing a historical log file, and a controller configured for, in response to an input from the user, instructing the neurostimulator to serially convey electrical stimulation energy to the one or more electrodes in accordance with the plurality of stimulation parameter sets, and logging the plurality of stimulation parameter sets in the historical log file. The user interface, memory, and controller may create and manipulate the historical log file in the same manner described above. The neurostimulation system may further comprise an external control device including a housing containing the user interface, the memory, and the controller.

In accordance with a third aspect of the present inventions, a method for providing therapy to a patient is provided. The method comprises defining a plurality of stimulation parameter sets, and serially conveying electrical stimulation energy to tissue of the patient in accordance with the plurality of stimulation parameter sets (e.g., at least one includes at least one of a pulse amplitude, a pulse width, a pulse rate, and an electrode combination). In one method, each of the plurality of stimulation parameter sets includes fractionalized electrical current values respectively for a plurality of electrodes, in which case, the method may further comprise displaying a graphical representation of the plurality of electrodes, and displaying the fractionalized electrical current values in association with the graphical representation of the plurality of electrodes.

The method further comprises storing a historical log file, and logging the plurality of stimulation parameter sets in the historical log file. An optional method further comprises logging temporal stamps (e.g., a time stamp and/or date stamp), relative to a start of a therapeutic procedure, or in the historical log file respectively indicating when the plurality of stimulation parameter sets were defined. The temporal stamps may be absolute or may be relative to a start of a therapeutic procedure. The method may further comprise serially conveying electrical stimulation energy to tissue of the patient in accordance with another plurality of stimulation parameter sets, and preventing the other plurality of stimulation parameter sets from being logged in the historical log file.

One method further comprises displaying the historical log file. In this case, the displayed historical log file may include serial numbers respectively associated with the logged stimulation parameter sets, and corresponding to the order in which the stimulation parameter sets were defined. The displayed historical log file may also include an information icon associated with each of the logged stimulation parameter sets. In this case, the method may further comprise selecting one of the information icons, and accessing additional information respectively associated with the selected information icon.

Another optional method further comprises selecting one of the logged stimulation parameter sets from the historical log file, and conveying electrical stimulation energy to the tissue of the patient in accordance with selected stimulation parameter set. The logged stimulation parameter set immediately prior to the stimulation parameter set in accordance with which the electrical stimulation energy is conveyed may be selected from the historical log file or the logged stimulation parameter set immediately subsequent to the stimulation parameter set in accordance with which the electrical stimulation energy is conveyed may be selected from the historical log file. Another method further comprises defining a plurality of predicted stimulation regions relative to the at least one electrode respectively corresponding to the plurality of stimulation parameter sets, displaying the historical log file as a trace that spatially connects points respectively corresponding to the predicted stimulation regions, and selecting the logged stimulation parameter set from the displayed trace.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present invention are obtained; a more particular description of the present invention briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE EMBODIMENTS

The description that follows relates to spinal cord stimulation (SCS) system. However, it is to be understood that the while the invention lends itself well to applications in SCS, the invention, in its broadest aspects, may not be so limited. Rather, the invention may be used with any type of implantable electrical circuitry used to stimulate tissue. For example, the present invention may be used as part of a pacemaker, a defibrillator, a cochlear stimulator, a retinal stimulator, a stimulator configured to produce coordinated limb movement, a cortical stimulator, a deep brain stimulator, peripheral nerve stimulator, microstimulator, or in any other neural stimulator configured to treat urinary incontinence, sleep apnea, shoulder sublaxation, headache, etc.

Figure 1:
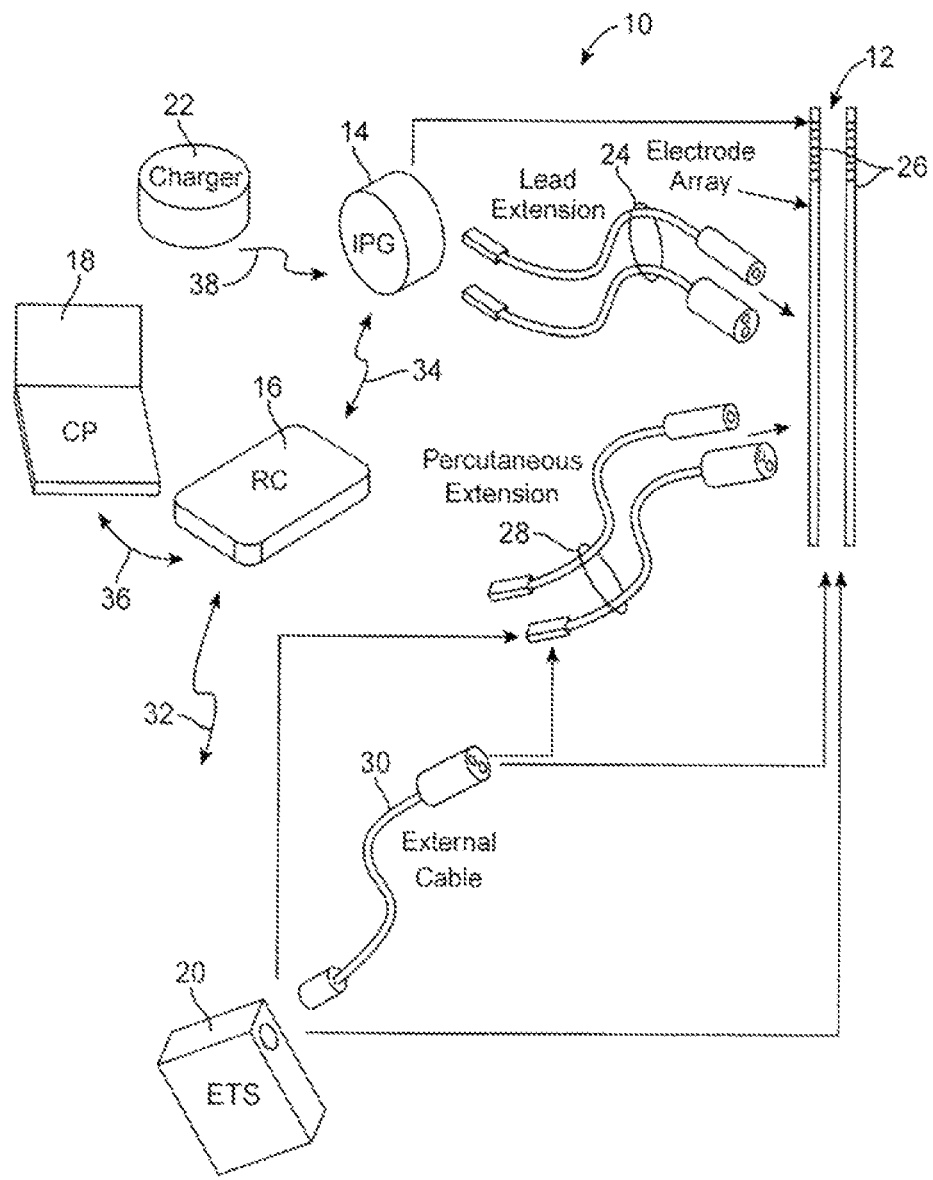
FIG. 1 is a plan view of a Spinal Cord Stimulation (SCS) system constructed in accordance with one embodiment of the present invention.

Turning first to FIG. 1, an exemplary SCS system 10 generally includes a plurality (in this case—two) of implantable neurostimulation leads 12, an implantable pulse generator (IPG) 14, an external remote controller RC 16, a clinician's programmer (CP) 18, an external trial stimulator (ETS) 20, and an external charger 22.

The IPG 14 is physically connected via one or more percutaneous lead extensions 24 to the neurostimulation leads 12, which carry a plurality of electrodes 26 arranged in an array. In the illustrated embodiment, the neurostimulation leads 12 are percutaneous leads, and to this end, the electrodes 26 are arranged in-line along the neurostimulation leads 12. Alternatively, a surgical paddle lead can be used in place of or in addition to the percutaneous leads. As will be described in further detail below, the IPG 14 includes pulse generation circuitry that delivers electrical stimulation energy in the form of a pulsed electrical waveform (i.e., a temporal series of electrical pulses) to the electrode array 26 in accordance with a set of stimulation parameters.

The ETS 20 may also be physically connected via the percutaneous lead extensions 28 and external cable 30 to the neurostimulation leads 12. The ETS 20, which has similar pulse generation circuitry as the IPG 14, also delivers electrical stimulation energy in the form of a pulse electrical waveform to the electrode array 26 in accordance with a set of stimulation parameters. The major difference between the ETS 20 and the IPG 14 is that the ETS 20 is a non-implantable device that is used on a trial basis after the neurostimulation leads 12 have been implanted and prior to implantation of the IPG 14, to test the responsiveness of the stimulation that is to be provided. Thus, any functions described herein with respect to the IPG 14 can likewise be performed with respect to the ETS 20.

The RC 16 may be used to telemetrically control the ETS 20 via a bi-directional RF communications link 32. Once the IPG 14 and neurostimulation leads 12 are implanted, the RC 16 may be used to telemetrically control the IPG 14 via a bi-directional RF communications link 34. Such control allows the IPG 14 to be turned on or off and to be programmed with different stimulation parameter sets. The IPG 14 may also be operated to modify the programmed stimulation parameters to actively control the characteristics of the electrical stimulation energy output by the IPG 14. As will be described in further detail below, the CP 18 provides clinician detailed stimulation parameters for programming the IPG 14 and ETS 20 in the operating room and in follow-up sessions.

The CP 18 may perform this function by indirectly communicating with the IPG 14 or ETS 20, through the RC 16, via an IR communications link 36. Alternatively, the CP 18 may directly communicate with the IPG 14 or ETS 20 via an RF communications link (not shown). The clinician detailed stimulation parameters provided by the CP 18 are also used to program the RC 16, so that the stimulation parameters can subsequently be modified by operation of the RC 16 in a stand-alone mode (i.e., without the assistance of the CP 18).

The external charger 22 is a portable device used to transcutaneously charge the IPG 14 via an inductive link 38. For purposes of brevity, the details of the external charger 22 will not be described herein. Once the IPG 14 has been programmed and its power source has been charged by the external charger 22 or otherwise replenished, the IPG 14 may function as programmed without the RC 16 or CP 18 being present. For purposes of brevity, the details of the IPG 14, ETS 20, and external charger 22 will not be described herein. Details of exemplary embodiments of these devices are disclosed in U.S. Pat. No. 6,895,280, which is expressly incorporated herein by reference.

Figure 2:
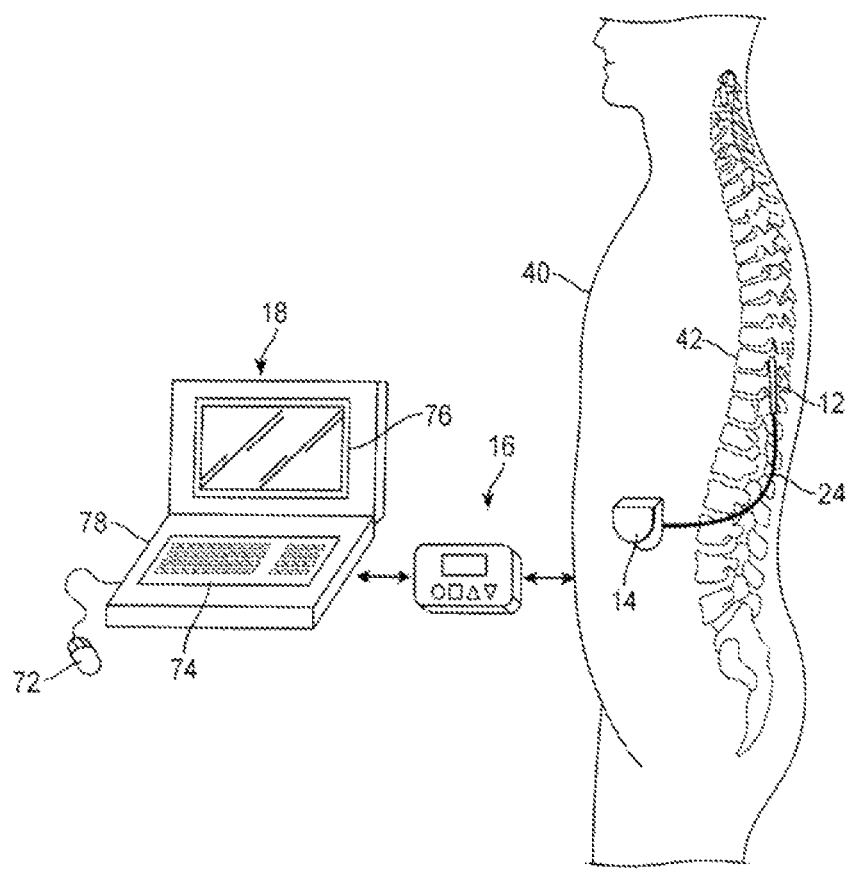
FIG. 2 is a plan view of the SCS system of FIG. 1 in use with a patient.

As shown in FIG. 2, the neurostimulation leads 12 are implanted within the spinal column 42 of a patient 40. The preferred placement of the neurostimulation leads 12 is adjacent, i.e., resting over, the spinal cord area to be stimulated. Due to the lack of space near the location where the neurostimulation leads 12 exits the spinal column 42, the IPG 14 is generally implanted in a surgically-made pocket either in the abdomen or above the buttocks. The IPG 14 may, of course, also be implanted in other locations of the patient's body. The lead extension 24 facilitates locating the IPG 14 away from the exit point of the neurostimulation leads 12. As there shown, the CP 18 may communicate with the IPG 14 via the RC 16.

As shown in FIG. 2, the overall appearance of the CP 18 is that of a laptop personal computer (PC), and in fact, may be implemented as a PC that has been appropriately configured to include a directional-programming device and programmed to perform the functions described herein. Thus, the programming methodologies can be performed by executing software instructions contained within the CP 18. Generally, the software instructions may include but are not limited to routines, programs, objects, components, data structures, procedures, modules, functions, and the like that perform particular functions or implement particular abstract data types. These instructions may be stored on a computer readable medium and may be loaded in an appropriate device for execution. Alternatively, such programming methodologies can be performed using firmware or hardware. In any event, the CP 18 may actively control the characteristics of the electrical stimulation generated by the IPG 14 to allow the optimum stimulation parameters to be determined based on patient feedback and for subsequently programming the IPG 14 with the optimum stimulation parameters.

Figure 3:
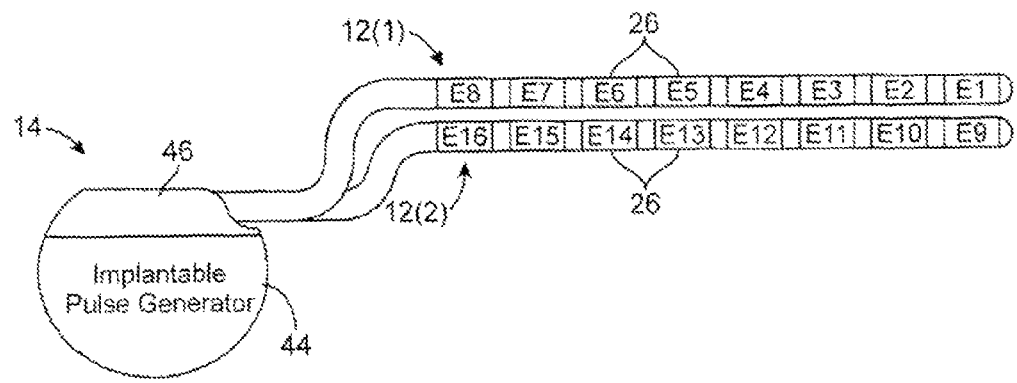
FIG. 3 is a profile view of an implantable pulse generator (IPG) and percutaneous leads used in the SCS system of FIG. 1.

Referring now to FIG. 3, the features of the neurostimulation leads 12 and the IPG 14 will be briefly described. One of the neurostimulation leads 12(1) has eight electrodes 26 (labeled E1-E8), and the other neurostimulation lead 12(2) has eight electrodes 26 (labeled E9-E16). The actual number and shape of leads and electrodes will, of course, vary according to the intended application. The IPG 14 includes an outer case 44 for housing the electronic and other components (described in further detail below). The outer case 44 is composed of an electrically conductive, biocompatible material, such as titanium, and forms a hermetically sealed compartment, wherein the internal electronics are protected from the body tissue and fluids. In some cases, the outer case 44 may serve as an electrode. The IPG 14 further includes a connector 46 to which the proximal ends of the stimulation leads 12 mate in a manner that electrically couples the electrodes 26 to the internal electronics (described in further detail below) within the outer case 44. To this end, the connector 46 includes one or more ports (in this embodiment, two ports (although not shown) for two percutaneous leads) for receiving the proximal end(s) of the neurostimulation leads 12. In the case, where the lead extensions 24 are used, the ports may instead receive the proximal ends of such lead extensions 24.

The IPG 14 includes a battery and pulse generation circuitry that delivers the electrical stimulation energy in the form of a pulsed electrical waveform to the electrode array 26 in accordance with a set of stimulation parameters programmed into the IPG 14. Such stimulation parameters may include electrode combinations, which define the electrodes that are activated as anodes (positive), cathodes (negative), or are turned off (zero). The parameters further include percentage of stimulation energy assigned to each electrode (fractionalized electrode configurations), and electrical pulse parameters, which define the pulse amplitude (measured in milliamps or volts depending on whether the IPG 14 supplies constant current or constant voltage to the electrode array 26), pulse width (measured in microseconds), and pulse rate (measured in pulses per second).

Electrical stimulation may occur between two (or more) activated electrodes, one of which may be the IPG case.

Stimulation energy may be transmitted to the tissue in a monopolar or multipolar (e.g., bipolar, tripolar, etc.) fashion. Monopolar stimulation occurs when a selected one of the lead electrodes 26 is activated along with the case of the IPG 14, so that stimulation energy is transmitted between the selected electrode 26 and case. Bipolar stimulation occurs when two of the lead electrodes 26 are activated as anode and cathode, so that stimulation energy is transmitted between the selected electrodes 26. For example, electrode E3 on the first lead 12 may be activated as an anode at the same time that electrode E11 on the second lead 12 is activated as a cathode. Tripolar stimulation occurs when three of the lead electrodes 26 are activated, two as anodes and the remaining one as a cathode, or two as cathodes and the remaining one as an anode. For example, electrodes E4 and E5 on the first lead 12 may be activated as anodes at the same time and electrode E12 on the second lead 12 is activated as a cathode.

In the illustrated embodiment, the IPG 14 can individually control the magnitude of electrical current flowing through each of the electrodes. In this case, it is preferred to have a current generator, wherein individual current-regulated amplitudes from independent current sources for each electrode 26 may be selectively generated. Although this system is optimized to take advantage of the invention, other stimulators that may be used with the invention include stimulators having voltage regulated outputs. While individually programmable electrode 26 amplitudes are optimized to achieve fine control, a single output source switched across electrodes 26 may also be used, although with less fine control in programming. Mixed current and voltage regulated devices may also be used with the invention. Further details discussing the detailed structure and function of IPGs are described more fully in U.S. Pat. Nos. 6,516,227 and 6,993,384, which are expressly incorporated herein by reference.

It should be noted that rather than an IPG, the SCS system 10 may alternatively utilize an implantable receiver-stimulator (not shown) connected to the neurostimulation leads 12. In this case, the power source, e.g., a battery, for powering the implanted receiver, as well as control circuitry to command the receiver-stimulator, will be contained in an external controller inductively coupled to the receiver-stimulator via an electromagnetic link. Data/power signals are transcutaneously coupled from a cable-connected transmission coil placed over the implanted receiver-stimulator. The implanted receiver-stimulator receives the signal and generates the stimulation in accordance with the control signals.

Figure 4:
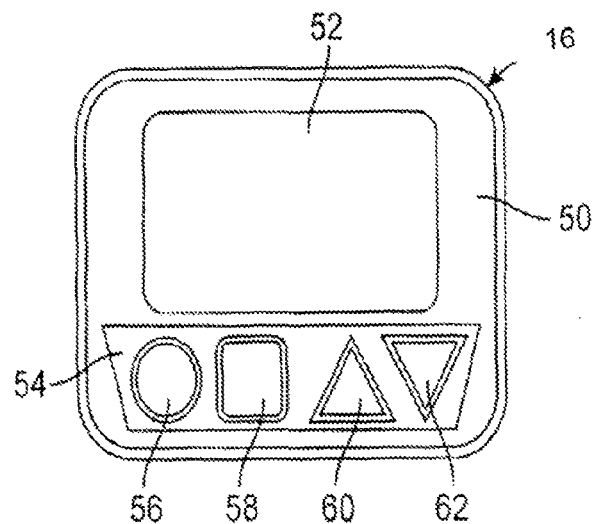
FIG. 4 is front view of a remote control (RC) used in the SCS system of FIG. 1.

Referring now to FIG. 4, one exemplary embodiment of the RC 16 will now be described. As previously discussed, the RC 16 is capable of communicating with the IPG 14, CP 18, or ETS 20. The RC 16 includes a casing 50, which houses internal components (including a printed circuit board (PCB)), a lighted display screen 52, and button pad 54 carried by the exterior of the casing 50. In the illustrated embodiment, the display screen 52 is a lighted flat panel display screen, and the button pad 54 includes a membrane switch with metal domes positioned over a flex circuit, and a keypad connector connected directly to a PCB. In an optional embodiment, the display screen 52 has touchscreen capabilities. The button pad 54 includes a multitude of buttons 56, 58, 60, and 62, which allow the IPG 14 to be turned ON and OFF, provide for the adjustment or setting of stimulation parameters within the IPG 14, and provide for selection between screens.

In the illustrated embodiment, the button 56 serves as an ON/OFF button that can be actuated to turn the IPG 14 ON and OFF. The button 58 serves as a select button that allows the RC 16 to switch between screen displays and/or parameters. The buttons 60 and 62 serve as up/down buttons that can be actuated to increment or decrement any of stimulation parameters including pulse amplitude, pulse width, and pulse rate of the pulse generated by the IPG 14. For example, the selection button 58 can be actuated to place the RC 16 in a "Pulse Amplitude Adjustment Mode," during which the pulse amplitude can be adjusted via the up/down buttons 60, 62, a "Pulse Width Adjustment Mode," during which the pulse width can be adjusted via the up/down buttons 60, 62, and a "Pulse Rate Adjustment Mode," during which the pulse rate can be adjusted via the up/down buttons 60, 62. Alternatively, dedicated up/down buttons 60, 62 can be provided for each stimulation parameter. Rather than using up/down buttons 60, 62, any other type of actuator, such as a dial, slider bar, or keypad, can be used to increment or decrement the stimulation parameters. Further details of the functionality and internal components of the RC 16 are disclosed in U.S. Pat. No. 6,895,280, which has previously been incorporated herein by reference.

Figure 5:
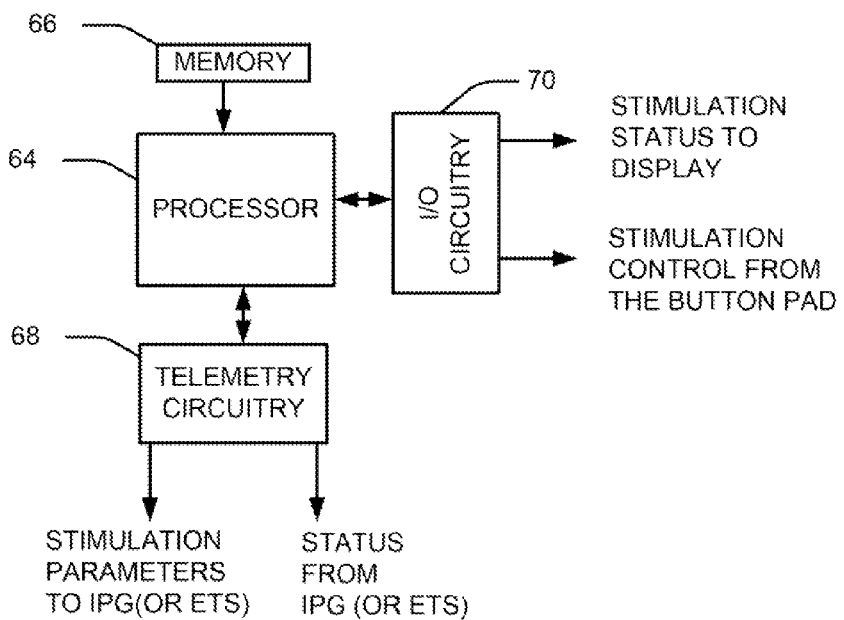
FIG. 5 is a block diagram of the internal components of the RC of FIG. 4.

Referring to FIG. 5, the internal components of an exemplary RC 16 will now be described. The RC 16 generally includes a processor 64 (e.g., a microcontroller), memory 66 that stores an operating program for execution by the processor 64, as well as stimulation parameter sets in a navigation table (described below), telemetry circuitry 68 for outputting stimulation parameters to the IPG 14 and receiving status information from the IPG 14, and input/output circuitry 70 for receiving stimulation control signals from the button pad 54 and transmitting status information to the display screen 52 (shown in FIG. 4). As well as controlling other functions of the RC 16, which will not be described herein for purposes of brevity, the processor 64 generates new stimulation parameter sets in response to the user operation of the button pad 54. These new stimulation parameter sets are then transmitted to the IPG 14 via the telemetry circuitry 68. Further details of the functionality and internal components of the RC 16 are disclosed in U.S. Pat. No. 6,895,280, which has previously been incorporated herein by reference.

In one embodiment, the user interface of the RC 16 may include a reset control (not shown). Upon actuation, the reset control allows the user to retrieve the original parameters from the memory 66 and instructs the IPG 14 to return to those original parameters. In this way, the user can switch from the experimental stimulation parameter sets created during the various programming sessions to the original stimulation parameter sets established at the initial fitting session for the IPG 14.

As briefly discussed above, the CP 18 greatly simplifies the programming of multiple electrode combinations, allowing the user (e.g., the physician or clinician) to readily determine the desired stimulation parameters to be programmed into the IPG 14, as well as the RC 16. Thus, modification of the stimulation parameters in the programmable memory 66 of the RC 16 after implantation is performed by a user using the CP 18, which can directly communicate with the IPG 14 or indirectly communicate with the IPG 14 via the RC 16. That is, the CP 18 can be used by the user to modify operating parameters of the electrode array 26 near the spinal cord.

Typically, a user (not shown) uses the CP 18 to program and manage neurostimulation therapy. Programming the therapy involves adjusting stimulation parameter sets (including electrical pulse parameters and/or electrode combinations) to optimize therapeutic effect. During a programming session, it is very common practice to go through and test many stimulation parameter sets with the patient 40. In the context of the present invention, the CP 18 is configured for logging and displaying the entire history of multiple stimulation parameter sets that were tested or attempted with the patient 40 during one or more programming sessions.

As shown in FIG. 2, the overall appearance of the CP 18 is that of a laptop personal computer (PC), and in fact, may be implemented using a PC that has been appropriately configured to include a directional-programming device and programmed to perform the functions described herein. Alternatively, the CP 18 may take the form of a mini-computer, personal digital assistant (PDA), etc., or even a remote control (RC) with expanded functionality. Thus, the programming methodologies can be performed by executing software instructions contained within the CP 18. Alternatively, such programming methodologies can be performed using firmware or hardware. In any event, the CP 18 may actively control the characteristics of the electrical stimulation generated by the IPG 14 to allow the optimum stimulation parameters to be determined based on patient feedback and for subsequently programming the IPG 14 with the optimum stimulation parameters To allow the user to perform these functions, the CP 18 includes a user input device (e.g., a mouse 72 and a keyboard 74), and a programming display screen 76 housed in a case 78. It is to be understood that in addition to, or in lieu of, the mouse 72, other directional programming devices may be used, such as a trackball, touchpad, joystick, or directional keys included as part of the keys associated with the keyboard 74.

In the illustrated embodiment described below, the display screen 76 takes the form of a conventional screen, in which case, a virtual pointing device, such as a cursor controlled by a mouse, joy stick, trackball, etc., can be used to manipulate graphical objects on the display screen 76. In alternative embodiments, the display screen 76 takes the form of a digitizer touch screen, which may either passive or active. If passive, the display screen 76 includes detection circuitry (not shown) that recognizes pressure or a change in an electrical current when a passive device, such as a finger or non-electronic stylus, contacts the screen. If active, the display screen 76 includes detection circuitry that recognizes a signal transmitted by an electronic pen or stylus. In either case, detection circuitry is capable of detecting when a physical pointing device (e.g., a finger, a non-electronic stylus, or an electronic stylus) is in close proximity to the screen, whether it be making physical contact between the pointing device and the screen or bringing the pointing device in proximity to the screen within a predetermined distance, as well as detecting the location of the screen in which the physical pointing device is in close proximity. When the pointing device touches or otherwise is in close proximity to the screen, the graphical object on the screen adjacent to the touch point is "locked" for manipulation, and when the pointing device is moved away from the screen the previously locked object is unlocked. Further details discussing the use of a digitizer screen for programming are set forth in U.S. Provisional Patent Application Ser. No. 61/561,760, entitled "Technique for Linking Electrodes Together during Programming of Neurostimulation System," which is expressly incorporated herein by reference.

Figure 6:
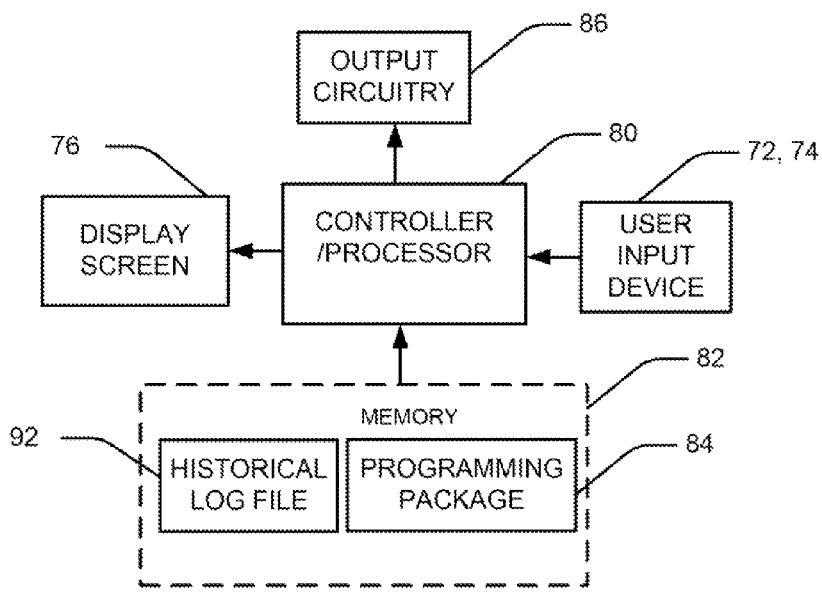
FIG. 6 is a block diagram of the internal components of a clinician's programmer (CP) used in the SCS system of FIG. 1.

As shown in FIG. 6, the CP 18 includes a controller/processor 80 (e.g., a central processor unit (CPU)) and memory 82 that stores a stimulation programming package 84, which can be executed by the controller/processor 80 to allow the user to program the IPG 14, and RC 16. The CP 18 further includes output circuitry 86 (e.g., via the telemetry circuitry 68 of the RC 16) for downloading stimulation parameters to the IPG 14 and RC 16 and for uploading stimulation parameters already stored in the memory 66 of the RC 16, via the telemetry circuitry 68 of the RC 16. Notably, while the controller/processor 80 is shown in FIG. 6 as a single device, the processing functions and controlling functions can be performed by a separate controller and processor 64. Thus, it can be appreciated that the controlling functions described below as being performed by the CP 18 can be performed by a controller, and the processing functions described below as being performed by the CP 18 can be performed by the processor 64. Furthermore, although the controller/processor 80 and/or memory 82 are illustrated and described herein as being part of the CP 18, in other embodiments, the controller/processor 80 and/or memory 82 may be a part of the IPG 14 and further may be configured to communicate information to the CP 18 when these devices communicate with each other.

Execution of the programming package 84 by the controller/processor 80 provides a multitude of programming screens that can be navigated through. These programming screens allow the clinician, among other functions, to select or enter patient profile information (e.g., name, birth date, patient identification, physician, diagnosis, and address), enter procedure information (e.g., programming/follow-up, implant trial system, implant IPG, implant IPG and lead(s), replace IPG, replace IPG and leads, replace or revise leads, explant, etc.), generate a pain map of the patient, define the configuration and orientation of the leads, initiate and control the electrical stimulation energy output by the leads 12, and select and program the IPG 14 with stimulation parameters in both a surgical setting and a clinical setting. Further details discussing the above-described CP functions are disclosed in U.S. patent application Ser. No. 12/501,282, entitled "System and Method for Converting Tissue Stimulation Programs in a Format Usable by an Electrical Current Steering Navigator," and U.S. patent application Ser. No. 12/614,942, entitled "System and Method for Determining Appropriate Steering Tables for Distributing Stimulation Energy Among Multiple Neurostimulation Electrodes," which are expressly incorporated herein by reference.

Memory 82 may be any volatile, non-volatile, fixed, removable, magnetic, optical, or electrical media, such as a RAM, ROM, CD-ROM, hard disk, removable magnetic disk, memory cards or sticks, NVRAM, EEPROM, flash memory, and the like. The controller/processor 80 may include a microprocessor, a controller, a digital signal processor (DSP), an application specific integrated circuit (ASIC), a field programmable gate array (FPGA), or other discrete or integrated logic circuitry.

Significant to the present invention, the controller/processor 80 is configured for storing in the memory 82 a historical log file 92 that logs the entire history of multiple stimulation parameter sets that were tested with the patient 40 during one or more programming sessions. The programming history is updated in the historical log file 92 based on retesting of the stimulation parameter sets during a follow-up programming session. In particular, every single change (whether incremental or decremental) to a tested stimulation parameter set is logged by the CP 18 in the historical log file 92; each with a temporal stamp (as will be discussed later in detail).

The stored log file 92 is displayed to the user via the display screen 76. So, anytime during the programming session, the display screen 76 allows the user to scroll through and access any of the previously tested stimulation parameter sets (via a pointing device).

In particular, upon selection, the controller/processor 80 accesses that stimulation parameter set from the historical log file 92; defines the selected parameter set as the current parameter set; and instructs the IPG 14 to serially convey electrical stimulation energy to the electrodes 26 in accordance with the selected stimulation parameter set.

The historical log file 92 may be any machine and/or human readable file—text file, for example. The data stored in the historical log file 92 may be in the text format, but other formats for storing the data may also be contemplated. There may be a separate log file for each patient thereby making the log files patient specific. Further, the historical log file 92 may contain an initial data entry including at least the name and/or the identification number of a patient. The rest of the data entries may be sets of data blocks, each containing details of stimulation parameter sets along with the time and date information indicating when these stimulation parameter sets were defined.

Figure 7:
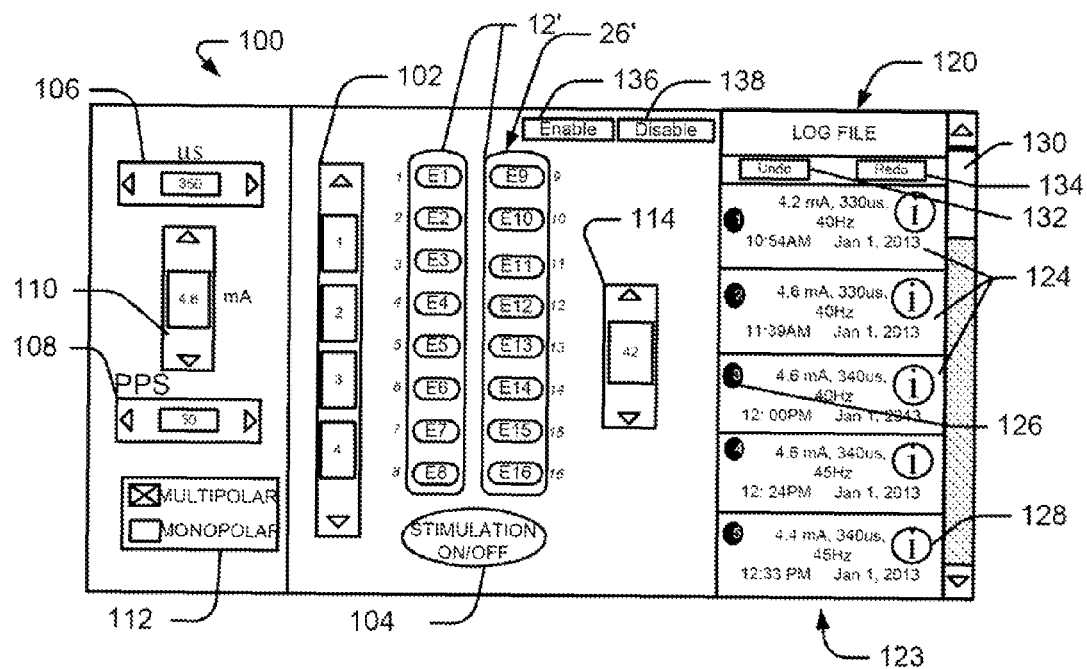
FIG. 7 is a plan view of a programming screen generated by the CP of FIG. 6 for programming the IPG of FIG. 3.

With reference now to FIG. 7, an exemplary programming screen 100 generated by the CP 18 to allow the user to program the IPG 14 will now be described. The programming screen 100 includes various controls described below that can be actuated to define a plurality of stimulation parameter sets and perform various control functions.

A pointing element may be used to graphically touch the controls to perform the actuation event or select a previous event for repetition. As described above, in the case of a digitizer touch screen, the pointing element can be an actual pointing element (e.g., a finger or active or passive stylus) to physically tap the screen above the respective graphical control or otherwise brought into proximity with respect to the control. In the case of a conventional screen, the pointing element will be a virtual pointing element (e.g., a cursor) that can be used to graphically click on the respective control. Any of the graphical controls described below may be actuated using a pointing element.

As shown, the exemplary programming screen 100 includes an electrode combination control 102 having arrows that can be actuated by the user to select one of four different electrode combinations 1-4. The programming screen 100 further includes stimulation on/off control 104 that can be alternately actuated to initiate or cease the delivery of electrical stimulation energy from the IPG 14 via the selected electrode combination.

The programming screen 100 allows the user to modify the characteristics (i.e., the electrical pulse parameters) of the stimulation energy output by the IPG 14 to the electrodes 26 by adjusting at least one of a pulse amplitude, pulse width, or pulse rate. Notably, the adjustment of the pulse width, pulse rate, and pulse amplitude may be performed globally for all of the electrodes 26 activated as either an anode (+) or a cathode (−). To this end, the programming screen 100 further includes various stimulation parameter controls that can be operated by the user to manually adjust stimulation parameters for the selected electrode combination. In particular, the programming screen 100 includes a pulse width adjustment control 106 (expressed in microseconds (μs)), a pulse rate adjustment control 108 that defines the pulses per second (PPS) (expressed in Hertz (Hz)), and a pulse amplitude adjustment control 110 (expressed in milliamperes (mA)). Each control includes a first arrow that can be actuated to incrementally decrease the value of the stimulation parameter and a second arrow that can be actuated to incrementally increase the value of the respective stimulation parameter. For instance, the pulse width adjustment control 106 is configured for controlling the pulse width of a stimulation current being output by the IPG 14. In some embodiments, the programming screen 100 may include fields for entering pulse width value, pulse rate value, and pulse amplitude value. In other embodiments, the programming screen 100 may include controls for other characteristics or aspects of the stimulation current, such as shape of the pulses or waveform of the stimulation current.

Each of the electrode combinations 1-4 can be created using various controls. In particular, the programming screen 100 displays graphical representations of the leads 12' including the electrodes 26'. In the illustrated embodiment, each electrode representation 26' takes the form of a closed geometric figure, in this case a rectangle. In alternative embodiments, the electrode representations 26' can take the form of other types of closed geometric figures, such as circles. The electrode representations 26' can be actuated multiple times to switch the corresponding active electrode 26 between an on-state, which includes either a positive polarity (anode) or a negative polarity (cathode), and an off-state. In essence, the electrode representations 26' themselves operate as the graphical controls, the actuations of which prompt the controller/processor 80 to assign the polarities to the selected electrodes 26. In alternative embodiments, the control that are separate from the electrode representations 26' may be used to change the polarity of the selected electrodes 26.

To enable selection between a multipolar configuration and a monopolar configuration, the programming screen 100 also includes multipolar/monopolar stimulation selection control 112, which includes check boxes that can be alternately activated by the user to selectively provide multipolar or monopolar stimulation. If a multipolar electrode arrangement is desired, at least one of the electrodes E1-E16 will be selected as an anode (+) and at least one other of the electrodes E1-E16 will be selected as a cathode (−). If a monopolar electrode arrangement is desired, none of the electrodes E1-E16 will be selected as an anode (+), and thus, the electrode representations 26' can only be actuated to toggle the corresponding electrode 26 between a cathode (−) and off (0).

The programming screen 100 further includes an electrode specific current adjustment control 114 that can be manipulated to independently vary stimulation amplitude values for the electrodes E1-E16. In particular, for each electrode selected to be activated as either a cathode or anode, the clinician can click on the upper arrow of the control 114 to incrementally increase the absolute value of the stimulation amplitude of the selected electrode, and the clinician can click on the lower arrow of the control 114 to incrementally decrease the absolute value of the stimulation amplitude of the selected electrode. The control 114 may also include an indicator that provides an alphanumeric indication of the stimulation amplitude currently assigned to the selected electrode. In an optional embodiment, non-alphanumeric indicators, such as different colors, different color luminance, different patterns, different textures, different partially-filled objects, etc., can be used to indicate the stimulation amplitude currently assigned to the selected electrodes, as discussed in U.S. patent application Ser. No. 13/200,629, entitled "Neurostimulation System and Method for Graphically Displaying Electrode Stimulation Values," which is expressly incorporated herein by reference.

In the illustrated embodiment, the stimulation amplitude values are fractionalized electrical current values (% current), such that the values for each polarization totals 100. However, in alternative embodiments, the stimulation amplitude values may be normalized current or voltage values (e.g., 1-10), absolute current or voltage values (e.g., mA or V), etc. Further, the stimulation amplitude values may be parameters that are a function of current or voltage, such as charge (current amplitude×pulse width) or charge injected per second (current amplitude×pulse width×rate (or period)).

In some alternative embodiments, a stimulation amplitude adjustment control (not shown) may appear next to the electrode representation 26' that can be touched or clicked, as described in U.S. patent application Ser. No. 13/200,629, which has been previously incorporated herein by reference, or may be superimposed over the electrode representation 26' that can be touched or clicked, as described in U.S. Provisional Patent Application Ser. No. 61/486,141, entitled "Neurostimulation System with On-Effector Programmer Control," which is expressly incorporated herein by reference. In another embodiment described in further detail below, the stimulation amplitude may be typed or written into a graphical data entry location associated with an electrode (e.g., next to or superimposed over the electrode representation 26').

The programming screen 100 further facilitates automated current steering; for example, by allowing the user to switch between a manual mode using the electrode selection and current adjustment techniques described above, an electronic trolling ("e-troll") mode that quickly sweeps the electrode array using a limited number of electrode configurations to gradually move a cathode in bipolar stimulation, and a Navigation programming mode that finely tunes and optimizes stimulation coverage for patient comfort using a wide number of electrode configurations, as described in U.S. Provisional Patent Application Ser. No. 61/576,924, entitled "Seamless Integration of Different Programming Modes for a Neurostimulator Programming System," which is expressly incorporated herein by reference. Virtual target poles may be utilized to steer the current within the electrode array, as described in U.S. Provisional Patent Application Ser. No. 61/452,965, entitled "Neurostimulation System for Defining a Generalized Virtual Multipole," which is expressly incorporated herein by reference.

In particular, the programming screen 100 includes a directional control device 116 (see FIG. 12) that represents the stimulation region along the spinal cord relative to the electrode array 26 that can be targeted using current shifting icons (i.e., up, down, left, and right arrows 115$a$, 115$b$, 115$c$, and 115$d$ respectively). The directional control device 116 has a horizontal bar 117 with a location designator 119 (represented by a rectangular opening) that indicates the current location of the stimulation region relative to the electrode array 26. Actuating the up and down arrows 115$a$, 115$b$ displaces the horizontal bar 117, and thus the location designator 119, up and down within the directional control device 116, and actuating the left and right arrows 115$c$, 115$d$ displaces the location designator 119 left and right along the horizontal bar 117. Thus, the stimulation region can be displaced upward by actuating the up arrow 115$a$, displaced downward by actuating the down arrow 115$b$, displaced to the left by actuating the left arrow 115$c$, and displaced to the right by actuating the right arrow 115$d$. The directional control device 116 displaces the stimulation region by steering the electrical current (i.e., shifting electrical current between the electrodes E1-E16) in a manner similar to that used by the E-Troll function described above to shift current between the electrodes E1-E16. Thus, actuating the up arrow 115$a$ displaces the cathode or cathodes upward in the electrode array, thereby displacing the stimulation region upward relative the spinal cord; actuating the down arrow 115$b$ displaces the cathode or cathodes downward in the electrode array, thereby displacing the stimulation region downward relative to the spinal cord; actuating the left arrow 115$c$ displaces the cathode or cathodes to the left in the electrode array, thereby displacing the stimulation region to the left relative to the spinal cord; and actuating the right arrow 115$d$ displaces the cathode or cathodes to the right in the electrode array, thereby displacing the stimulation region to the right relative to the spinal cord.

The directional control device 116 further includes a mark icon 118 that can be actuated to mark points 121. Each time when the horizontal bar 117 is moved in the desired location, the mark icon 118 is clicked to define the points 121. Each mark or point 121 is a set of stimulation parameters that corresponds to the location or area of the stimulation region. Further details related to the marks/points 121 are set forth in U.S. patent application Ser. No. 13/090,073, entitled "Neurostimulation System and Method with Adjustable Programming Rate," which is expressly incorporated herein by reference.

Significant to the present invention, the programming screen 100 of FIG. 7 includes a historical log file 120 that is displayed as a list having various stimulation parameter sets that were tested by the user during one or more stimulation programming sessions. Along with the stimulation parameter sets, the historical log file 120 stores temporal stamps for each stimulation parameter set, indicating when these parameter sets were defined or adjusted. The historical log file 120 can be accessed by the user through the user interface of the CP 18. The list 120 can be positioned anywhere on the screen 100. In the embodiment shown in FIG. 7, the historical log file 120 is shown as a window on the right hand side of the screen 100. Alternatively, the historical log file 120 can be represented in a different screen altogether, and the screen 100 can have a link to the different screen.

As mentioned above, the temporal stamp that includes time and date information is also logged for each stimulation parameter set. As seen from FIG. 7, the temporal stamp is absolute i.e., exact time (e.g., 10:54 AM) and date (e.g., Jan. 1, 2013) when the stimulation parameter sets were defined or adjusted. Alternatively, the time stamp can be relative to start of a therapeutic procedure and in such instances, time information for parameter sets may indicate a particular day, a particular hour, a particular minute since the start of the therapy, when the stimulation parameter sets were defined or adjusted. For example, assuming that the therapy starts at 8:00 AM, and now if the user defines a stimulation parameter set, the time information that will be logged along with the stimulation parameter set may be in the form of $7^{th}$ minute from the start of the therapy.

In another example, it can be considered that a patient visits a clinician on $8^{th}$ day since the start of the therapy and during the programming session on the $8^{th}$ day, the IPG 14 may be programmed by the CP 18 on a daily basis. Accordingly, the time information that will be logged along with stimulation parameter sets may be as day 1 of the session, day 2, day 3, and so on. Additionally, the stimulation parameter sets may be stored on the basis of morning sessions, noon sessions and evening sessions.

As shown, each stimulation parameter set along with the temporal stamp constitutes a stimulation event 124. If a stimulation event 124 in the historical log file 120 is retrieved, the settings from that event become the current setting and the settings are logged as a new event. As will be described in further detail below, later in the programming session, the user can go back to any of the logged stimulation events 124 for further testing. In the embodiment illustrated in FIG. 7, the programming screen 100 displays five stimulation events 124 being logged, and to view more stimulation events 124, the user can scroll the list 120 to see other stimulation events via actuation of a slide bar 130. In the preferred embodiment, adjustments to the stimulation parameter sets are saved to the list 120 as stimulation events 124 when the stimulation is on, but when the stimulation is off, then no adjustments to the stimulation parameter sets are saved in the list 120. In this manner, only stimulation parameters sets that are actually tested are logged in the list 120.

Figure 8A:
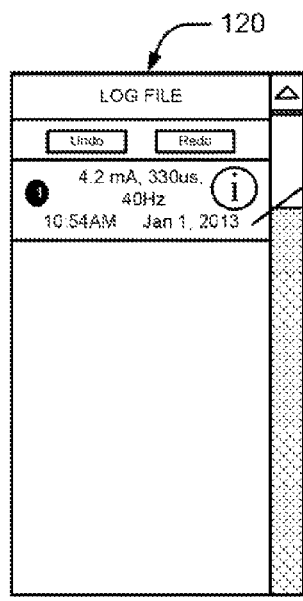
FIGS. 8A-8D are plan views of stimulation events logged to a historical log file stored by the CP of FIG. 6.
Figure 8B:
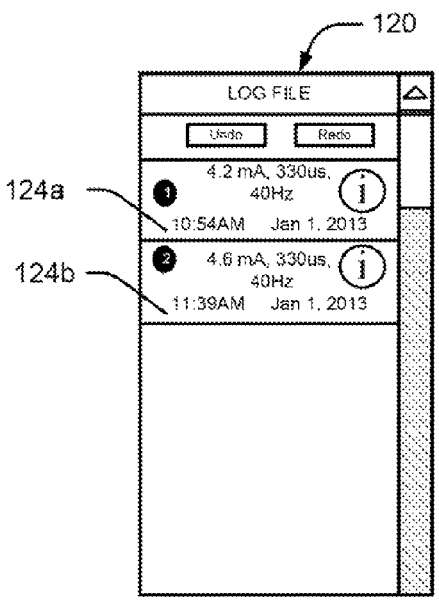
Figure 8C:
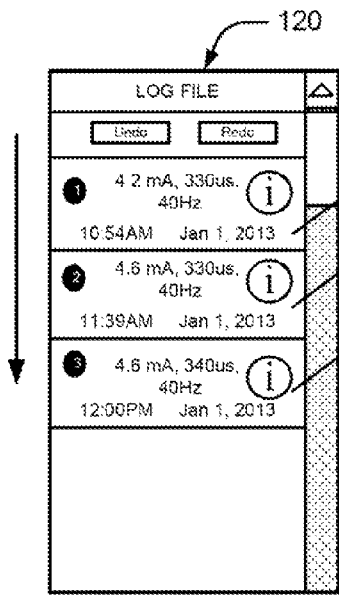
Figure 8D:
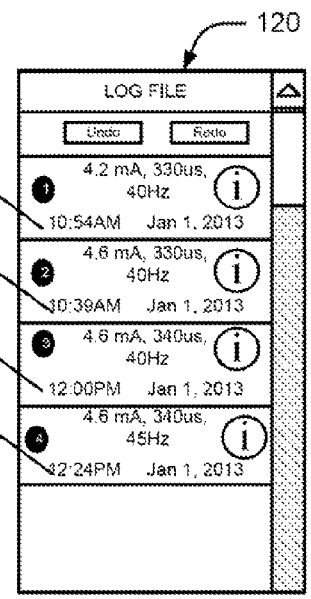

As shown in FIG. 7, the historical log file 120 records the information when there is a change to all or one or more stimulation parameters corresponding to a defined stimulation parameter set. That is, when the user defines or makes adjustments to any of the stimulation parameter sets, the controller/processor 80 logs that as a new stimulation event 124. For example, as shown in FIGS. 8A-8D, during a therapeutic procedure, a clinician can navigate through a large number of stimulation parameter sets to find the most effective stimulation parameter set. For instance, as shown in FIG. 8A, the user defines a parameter set with values, 4.2 mA, 330 µs, and 40 Hz at 10:54 AM on Jan. 1, 2013, which corresponds to a stimulation event 1 (124a). When the user changes amplitude value from 4.2 mA to 4.6 mA, but with other values remaining the same, this will be defined as the stimulation event 2 (124b), as shown in FIG. 8B. Similarly, as shown in FIGS. 8C and 8D, a stimulation event 3 (124c) is defined when the user changes pulse width value from 330 µs to 340 µs and a stimulation event 4 (124d) is defined the user changes pulse rate value from 40 Hz to 45 Hz. In addition to the electrical parameter sets, changes in the fractionalized electrode combinations will be considered stimulation events. All stimulation events will be logged in the historical log file 120.

Figure 9:
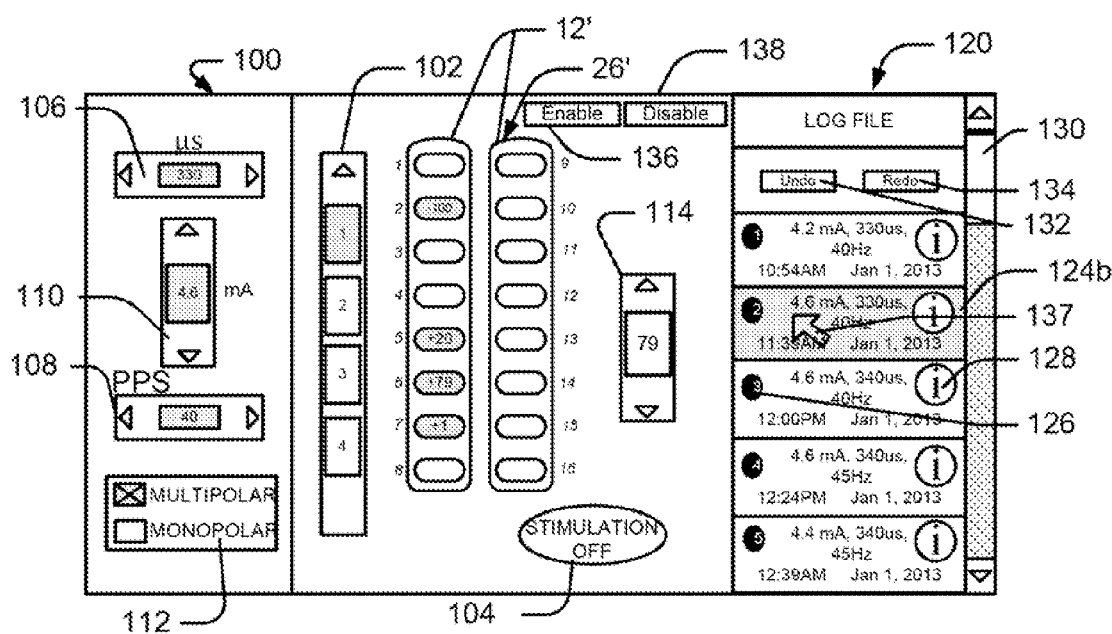
FIG. 9 illustrates the programming screen of FIG. 7, particularly showing the user selecting a stimulation event from the historical log file.

The programming screen 100 further includes a reset feature, where respective stimulation parameter values on the controls 106, 110, 108 are automatically reset to stimulation parameter values of a stimulation event 124, selected by the user. For example, upon selecting (e.g., via a cursor 137), the event 124b with parameter values—4.6 mA, 330 µs, and 40 Hz, respective stimulation parameter controls 110, 106, and 108 are automatically reset to define these values as clearly shown in the FIG. 9.

As seen from FIG. 7, the programming screen 100 displays the stimulation parameter sets in the order as they were defined by the user. The order is defined by serial numbers 126 corresponding to each stimulation parameter set. In other words, each stimulation parameter set is associated with a serial number 126 for representing the order in which they were defined. For instance, the stimulation parameter set corresponding to serial number "1" includes pulse amplitude 4.2 mA, pulse width 330 µs, and pulse rate 40 Hz. If the user makes any change to any of the above parameter values and that change is logged as the next stimulation event in order and will be associated with serial number "2". As seen from FIG. 7, adjustment to pulse amplitude is defined as next event in order. The serial numbers 126 can be arranged in ascending or descending order.

The programming screen 100 further includes enable and disable controls 136 and 138, respectively. Upon actuation of the enable control 136, the controller/processor 80 logs stimulation events 124 or stimulation parameter sets in the historical log file 120, whereas actuation of the disable control 138 prevents the controller/processor 80 from logging the stimulation events 124 in the historical log file 120. For instance, the user may activate the enable control 136 when testing various stimulation parameter sets with the patient 40. But if the user wishes not to log stimulation parameter sets during the testing, he may actuate the disable control 138.

The programming screen 100 further includes an information icon 128 associated with each stimulation parameter set or stimulation event 124 in the historical log file 120. Actuating the information icon 128 (e.g., by the cursor 137) allows the user to insert additional information about that stimulation event 124 in the historical log file 120. At a later time, the added information can be accessed by the user, upon selecting the information icon 128. In one example, the information icon 128 may allow the user to input comments associated with each stimulation parameter set describing how those parameters subjectively feel to the patient, e.g., the effectiveness and comfort of those particular stimulation parameter sets. Additionally, the user may insert additional information such as side effects, clinical assessments or notes, symptoms of patient through the information icon 128.

Figure 10A:
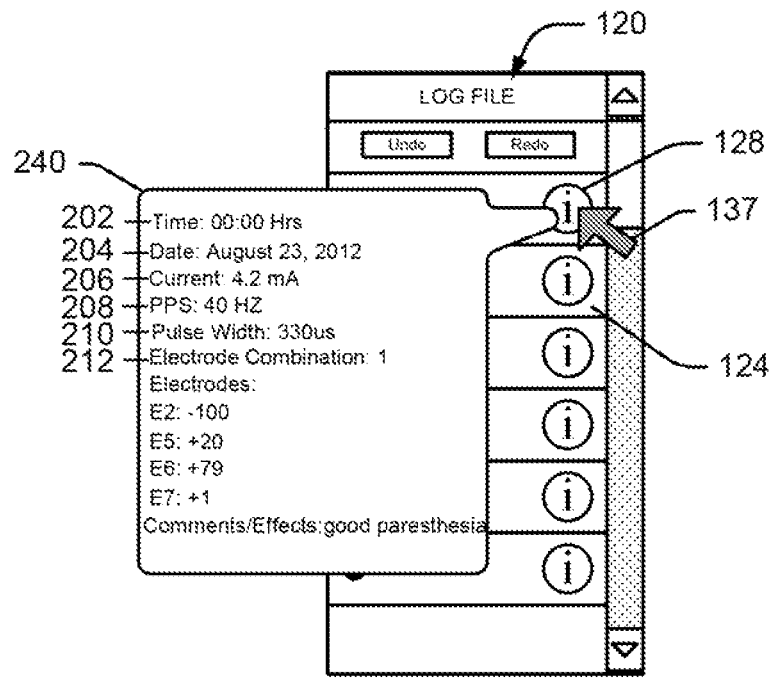
FIGS. 10A-10B show exemplary information boxes that appear upon actuating an information icon of the historical log file displayed in the programming screen of FIG. 9.
Figure 10B:
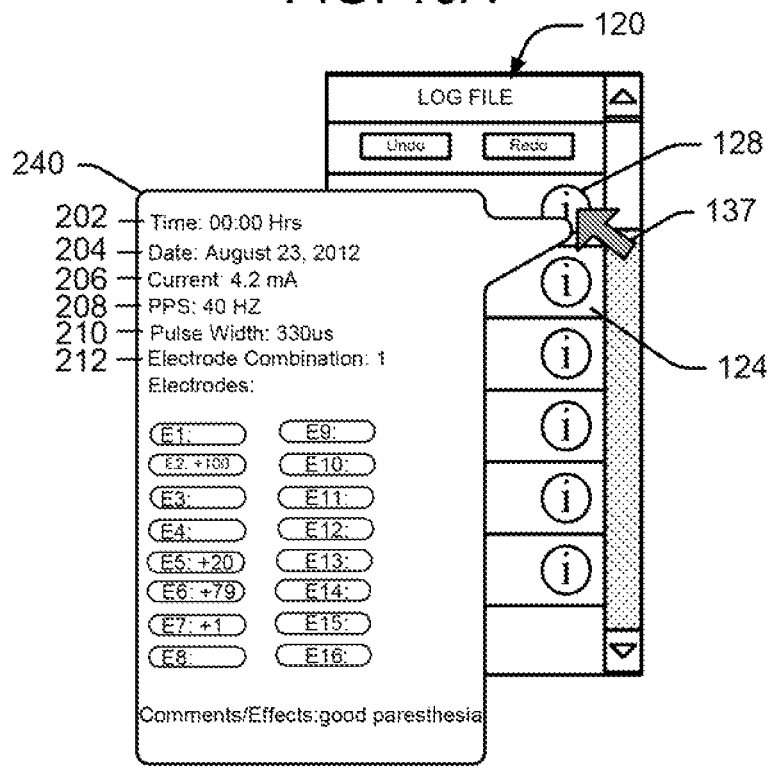

In the illustrated embodiment, an exemplary dialog box 240 is displayed upon actuating the information icon 128, as shown in FIG. 10A. The dialog box 240 provides detailed information associated with each stimulation parameter set, for example, the time 202 and date 204 when the electrical stimulation energy was delivered to the patient in accordance with the associated stimulation parameter set, as well as the associated stimulation parameters, such as the pulse amplitude 206, pulse rate 208, pulse width 210, and fractionalized electrode combination 212 (E2, E5, E6, and E7). As there shown, electrode E2 has a fractionalized cathodic current value of 100%, electrode E5 has a fractionalized anodic current value of 20%, electrode E6 has a fractionalized anodic current of 79%, and electrode E7 has a fractionalized anodic current value of 1%. Alternatively, as shown in FIG. 10B, the dialog box 240 depicts a graphical representation of the electrodes 26 along with fractionalized electrode current values with polarity for each electrode 26. Additionally, the dialog box 240 further displays comments input by the user that are associated with the stimulation parameter set. In this way, the information icon 128 assists the user in more quickly identifying one or more desirable parameter sets during a current programming session.

The programming screen 100 further includes redo and undo controls 134 and 132, respectively. These controls 134, 132 provide the user the ability to go back to any previously tested stimulation parameter sets during the programming session in an attempt to optimize the therapy. Also, these controls 134, 132 allow the user to easily navigate between the recent stimulation events 124 within the historical log file 120.

Figure 11A:
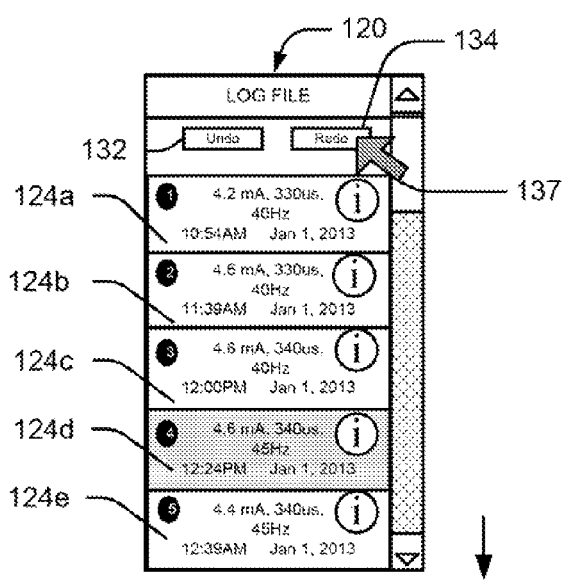
FIGS. 11A-11B are plan views of another programming screen that allows a user to undo or redo a stimulation event via the historical log file.
Figure 11B:
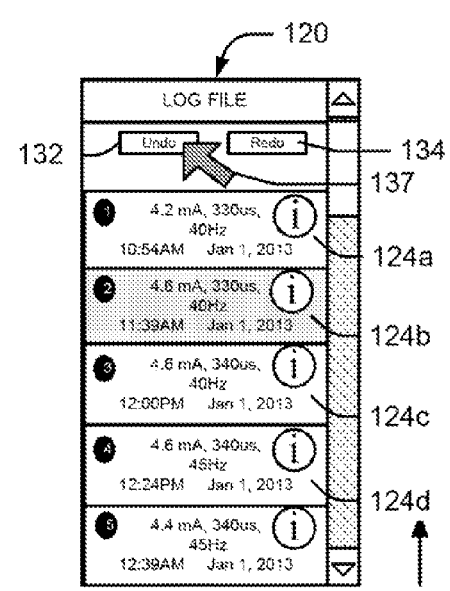

In particular, upon actuating the redo control 134, the controller/processor 80 selects the logged parameter set immediately defined subsequent to a stimulation parameter set currently defined by the stimulation parameter controls, as discussed above. For example, as shown in FIG. 11A, it can be assumed that current stimulation parameter set corresponds to a stimulation event at serial no. 3, and now when the user actuates the redo control 134 (e.g., by the cursor 137), the stimulation parameter set defined at serial no. 4 will be defined as the current parameter set by the CP 18. Similarly, upon actuating the undo control 132, the controller/processor 80 selects the stimulation parameter set immediately defined prior to a stimulation parameter set currently defined by the stimulation parameter controls. For example, as shown in FIG. 11B, it can be assumed that the current stimulation parameter set corresponds to a stimulation event at serial no. 3, and now when the user actuates the undo control 132 (e.g., by the cursor 137), the stimulation parameter set defined at serial no. 2 will be defined as the current parameter set by the CP 18. In some embodiments, undo and redo actions can be performed by a keyboard shortcut.

In an optional embodiment, controls (not shown) can be actuated to play forward or play reverse at variable speeds (e.g., fast and slow), and pause relative to a selected stimulation parameter set in the historical log file 120. For example, actuation of the play forward control (e.g., by continuously holding down or pressing the control or actuating the control once) automatically passes through the stimulation parameter sets stored in the historical log file in order, while actuation of the play reverse control (e.g., by continuously holding or pressing the control or actuating the control once) automatically passes through stimulation parameter sets stored in the historical log file in reverse order. Actuation of the pause control temporarily halts the play forward or play reverse process until the play forward control and/or play reverse control is actuated again.

Figure 12:
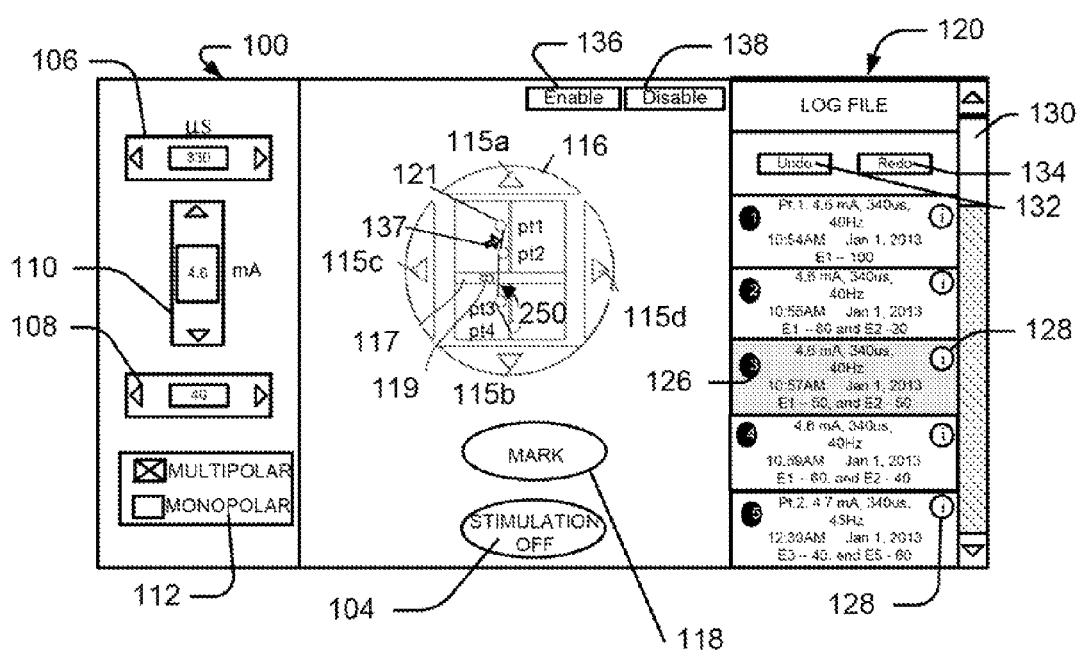
FIG. 12 is a plan view of another programming screen generated by the CP of FIG. 6 for programming the IPG of FIG. 3.

With reference to FIG. 12, the programming screen 100 further displays the historical log file 120 as a trace 250 of stimulation parameter sets (e.g., fractionalized electrode combinations in this case) that are generated by the directional control device 116 (discussed above in detail). As shown, the trace 250 represents the location of the predicted stimulation region as it is steered relative to the electrode array 26, and includes all marked points 121 (e.g., pt1, pt2, pt3, and pt4) that have been created via actuation of the marking icon 118, as well as any unmarked regions. The marked points 121 can be regions of interest for the user that correspond to stimulation parameter sets on which the patient 40 is having good effect, whereas the unmarked regions correspond to any region falling between the points 121. These marked points 121 and umarked regions both will be stored in the historical log file 120. If the user selects any point along the trace 250 (e.g., using the cursor 137), the corresponding stimulation parameter set (including fractionalized electrode combinations) will be defined as the current stimulation parameter set. Thus, by selecting any point along the trace 250, the historical log file 120 allows the user to get back to that corresponding stimulation parameter set. In the case where the resolution of the fractionalized electrode generation combination is so fine that logging of every fractionalized electrode generation combination would be impractical, only certain ones in the series of the fractionalized electrode combinations (e.g., every Nth fractionalized electrode combination) may be logged in the historical log file 120.

Although the foregoing techniques have been described as being implemented in the CP 18, it should be noted that this technique may alternatively or additionally be implemented in the RC 16. Furthermore, although particular embodiments of the present invention have been shown and described, it will be understood that it is not intended to limit the present invention to the preferred embodiments, and it will be obvious to those skilled in the art that various changes and modifications may be made without departing from the spirit and scope of the present invention. Thus, the present invention is intended to cover alternatives, modifications, and equivalents, which may be included within the spirit and scope of the present invention as defined by the claims.

What is claimed is:

1. An external control device for use with a neurostimulator coupled to one or more electrodes implanted within tissue, comprising:
    a user interface including a display screen and one or more stimulation parameter controls configured for being actuated by a user to define stimulation parameter sets;
    memory configured for storing a historical log file of stimulation events including stimulation parameter sets for the stimulation events, the historical log file including stimulation parameter values associated with respective stimulation parameters sets, the display screen configured for displaying the historical log file of stimulation events including the stimulation parameter values for the stimulation parameter sets; and
    a controller configured for, in response to an input from the user, instructing the neurostimulator to serially convey electrical stimulation energy to the one or more electrodes in accordance with the stimulation parameter sets, wherein the controller is configured to log a new stimulation event in the historical log file when the user input defines or makes adjustments to the parameter sets, including logging stimulation parameter values for the new stimulation event in the historical log file,
    wherein the controller is configured for togging temporal stamps in the historical log file respectively indicating when the plurality of stimulation parameter sets were defined and for displaying on the display screen the temporal stamps with their respective stimulation parameter set in the displayed historical log file of stimulation events,
    wherein the device is configured to display on the display screen serial identifiers respectively associated with the stimulation parameter sets in the historical log file, the serial identifiers being different than the temporal stamps and providing a serial representation of the order in which the stimulation parameter sets were defined, and
    wherein the device is configured to display information icons associated with respective stimulation events in the displayed historical log file of stimulation events, wherein each information icon is selectable to display the stimulation parameter values associated with the respective stimulation event.

2. The external control device of claim 1, wherein each information icon is selectable to display values selected from a group of values consisting of: a pulse amplitude value, a pulse width value, and a pulse rate value associated with the respective stimulation events.

3. The external control device of claim 1, wherein the one or more electrodes comprises a plurality of electrodes, each of the plurality of stimulation parameter sets includes fractionalized electrical current values respectively for the electrodes, and each information icon is selectable to display a graphical representation of the plurality of electrodes, and display the fractionalized electrical current values with the graphical representation of the plurality of electrodes.

4. The external control device of claim 1, wherein the temporal stamps are absolute.

5. The external control device of claim 1, wherein the temporal stamps are relative to a start of a therapeutic procedure.

6. The external control device of claim 1, wherein each of the temporal stamps is at least one of a time stamp and a date stamp.

7. The external control device claim 1, wherein the user interface includes an enable/disable control configured for being actuated by the user to selectively allow the controller to log the plurality of stimulation parameter sets in the historical log file or prevent the controller from logging the plurality of stimulation parameter sets in the historical log file.

8. The external control device of claim 1, wherein each information icon is selectable to display a dialog box to access additional information including comments respectively associated with the respective logged stimulation parameter set, the dial box includes stimulation parameter values respectively associated with respective stimulation events.

9. The external control device of claim 8, wherein each information icon is selectable to allow the user to add additional information associated with the respective logged stimulation parameter set.

10. The external control device of claim 1, wherein the user interface is further configured for allowing the user to select one of the logged stimulation parameter sets, and the controller is further configured for, in response to the selected logged stimulation parameter set, automatically resetting the one or more stimulation parameter controls to define the selected logged stimulation parameter set.

11. The external control device of claim 10, wherein the user interface includes a display screen configured for displaying the historical log file as a list, and the user interface is configured for allowing the user to select the logged stimulation parameter set from the displayed list with a pointing device.

12. The external control device of claim 10, wherein the user interface includes an undo control, the actuation of which selects the logged stimulation parameter set immediately defined prior to a stimulation parameter set currently defined by the one or more stimulation parameter controls.

13. The external control device of claim 10, wherein the user interface includes a redo control, the actuation of which selects the logged stimulation parameter set immediately defined subsequent to a stimulation parameter set currently defined by the one or more stimulation parameter controls.

14. The external control device of claim 10, wherein the user interface includes a directional control device, the actuation of which defines a plurality of predicted stimulation regions relative to the at least one electrode respectively corresponding to the plurality of stimulation parameter sets, the user interface further includes a display screen configured for displaying the historical log file as a trace that spatially connects points respectively corresponding to the predicted stimulation regions, and the user interface is configured for allowing the user to select the logged stimulation parameter set from the displayed trace with a pointing device.

15. The external control device of claim 1, further comprising output circuitry configured for transmitting instructions to the neurostimulator.

16. An external control device for use with a neurostimulator coupled to a plurality of electrodes implanted within tissue, comprising:
   a user interface including a display screen and one or more stimulation parameter controls configured for being actuated by a user to define stimulation parameter sets for testing during one or more stimulation programming sessions;
   memory configured for storing a historical log of stimulation events including stimulation parameter sets for the stimulation events, the historical log including stimulation parameter values associated with respective stimulation parameter sets, the display screen configured for displaying the historical log of stimulation events including the stimulation parameter values for the stimulation parameter sets; and
   a controller configured for, in response to an input from the user to test a newly defined or adjusted parameter set to be tested, logging the newly defined or adjusted parameter set as a new stimulation event in the historical log along with a temporal stamp indicating when the parameter set was defined or adjusted,
   wherein the device is configured to display with the historical log on the display screen:
      the stimulation parameter sets tested during one or more stimulation programming sessions,
      temporal information indicating when each of the parameter sets was defined or adjusted,
      serial identifiers associated with the logged stimulation parameter sets, the serial identifiers being different than the temporal information and providing a serial representation of the order in which the stimulation parameter sets were logged into the historical log of stimulation events, and
      an information icon associated with each of the stimulation parameter sets, wherein the information icon for a respective stimulation parameter set is selectable to display a dialog box that includes:
         comments associated with the respective stimulation parameter set;
         a pulse amplitude value associated with the respective parameter set;
         a pulse width value associated with the respective parameter set;
         pulse rate value associated with the respective parameter set; and
         fractionalized electrical current values with a graphical representation of the plurality of electrodes associated with the respective parameter set.

17. The external control device of claim 16, wherein the temporal stamps are absolute.

18. The external control device of claim 16, wherein the temporal stamps are relative to a start of a therapeutic procedure.

19. The external control device of claim 16, wherein each of the temporal stamps is at least one of a time stamp and a date stamp.

20. The external control device of claim 16, wherein the comments accessed through the dialog box includes:
   subjective feelings of the patient associated with the respective parameter set, or
   side effects, or
   clinical assessments or notes, or
   patient symptoms.

* * * * *